United States Patent
Schadewaldt et al.

(10) Patent No.: US 11,883,231 B2
(45) Date of Patent: Jan. 30, 2024

(54) ULTRASOUND IMAGING SYSTEM AND METHOD

(71) Applicant: KONINKLIJKE PHILIPS N.V., Eindhoven (NL)

(72) Inventors: Nicole Schadewaldt, Norderstedt (DE); Cristian Lorenz, Hamburg (DE); Alexander Schmidt-Richberg, Hamburg (DE); Tobias Klinder, Uelzen (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 638 days.

(21) Appl. No.: 17/045,215

(22) PCT Filed: Mar. 28, 2019

(86) PCT No.: PCT/EP2019/057822
§ 371 (c)(1),
(2) Date: Oct. 5, 2020

(87) PCT Pub. No.: WO2019/192918
PCT Pub. Date: Oct. 10, 2019

(65) Prior Publication Data
US 2021/0161508 A1 Jun. 3, 2021

(30) Foreign Application Priority Data
Apr. 5, 2018 (EP) .................................... 18165839

(51) Int. Cl.
*A61B 8/08* (2006.01)
*A61B 8/06* (2006.01)
*A61B 8/00* (2006.01)

(52) U.S. Cl.
CPC .............. *A61B 8/0866* (2013.01); *A61B 8/06* (2013.01); *A61B 8/0883* (2013.01); *A61B 8/483* (2013.01);
(Continued)

(58) Field of Classification Search
CPC ....... A61B 8/0866; A61B 8/06; A61B 8/0883; A61B 8/483; A61B 8/488; A61B 8/5215;
(Continued)

(56) References Cited

U.S. PATENT DOCUMENTS

2007/0249935 A1* 10/2007 Deschinger .......... A61B 8/0866
600/437
2007/0276214 A1* 11/2007 Dachille ................ G16H 30/40
600/407
(Continued)

OTHER PUBLICATIONS

International Search Report and Written Opinion for International Application No. PCT/EP2019/057822, filed Mar. 28, 2019, 14 pages.
(Continued)

*Primary Examiner* — Bo Joseph Peng

(57) ABSTRACT

A system for generating ultrasound data in respect of an anatomical body being scanned makes use of a predetermined scan protocol, which specifies a sequence of types of ultrasound scan of structures of interest. These types may for example be different imaging modalities (static, dynamic, 2D, 3D etc.) which are most appropriate for viewing different structures within the anatomical body. From received ultrasound images, a model is used to identify the structures of interest within the ultrasound images. The best images for creating the types of scan of the protocol are then identified and a sequence is compiled of those best images. In this way, a sequence is created which combines different types of scan, in a structured way according to a predetermined (Continued)

protocol. This makes the analysis of the sequence most intuitive for a user, and simplifies comparison between different sequences.

20 Claims, 3 Drawing Sheets

(52) U.S. Cl.
CPC ............ *A61B 8/488* (2013.01); *A61B 8/5215* (2013.01); *A61B 8/565* (2013.01)

(58) Field of Classification Search
CPC ....... A61B 8/565; A61B 8/5223; A61B 8/465; A61B 8/468; A61B 8/523; G06T 7/0012; G06T 2207/10132; G06T 2207/20084; G06T 2207/30044; G09B 23/286; G16H 30/20; G16H 40/63; G01S 7/52098; G01S 7/52074

See application file for complete search history.

(56) References Cited

U.S. PATENT DOCUMENTS

| | | |
|---|---|---|
| 2008/0051654 A1 | 2/2008 | Osumi et al. |
| 2011/0196235 A1 | 8/2011 | Dunbar et al. |
| 2011/0201935 A1 | 8/2011 | Collet-Billon et al. |
| 2013/0163838 A1 | 6/2013 | Barr et al. |
| 2013/0190600 A1* | 7/2013 | Gupta .................. A61B 8/0866 600/407 |
| 2015/0051489 A1 | 2/2015 | Caluser et al. |
| 2015/0190112 A1 | 7/2015 | Yeo et al. |
| 2016/0038121 A1 | 2/2016 | Waechter-Stehle et al. |
| 2017/0235903 A1 | 8/2017 | McLaughlin et al. |
| 2018/0092629 A1* | 4/2018 | Yoneyama ............... A61B 8/06 |

OTHER PUBLICATIONS

Baumgartner, et al., "Real-time Standard Scan Plane Detection and Localisation in Fetal Ultrasound using Fully Convolutional Neural Networks", Imperial College London, Department of Computing, MICCAI 2006, 8 pages.

Schmidt-Richberg, et al., "Abdomen segmentation in 3D fetal ultrasound using CNN-powered deformable models", submitted to MICCAI—workshop on Fetal and Infant analysis, (FIFI) 2017, pp. 52-61. (Abstract).

Parsai, et al., "Remote Sonographic Interpretation: Comparison of Standardized Video Clips to Still Images", vol. 40, No. 8, Oct. 2012, Journal of Clinical Ultrasound, pp. 495-501.

\* cited by examiner

ULTRASOUND IMAGING SYSTEM AND METHOD

RELATED APPLICATIONS

This application is the U.S. National Phase application under 35 U.S.C. § 371 of International Application No. PCT/EP2019/057822, filed on Mar. 28, 2019, which claims the benefit of European Application No. 18165839.4, filed Apr. 5, 2018. These applications are hereby incorporated by reference herein.

FIELD OF THE INVENTION

This invention relates to a system, method and computer program for generating ultrasound (US) data in respect of an anatomical body being scanned. It is especially, but not exclusively, useful for generating sequences of images of a human fetus.

BACKGROUND OF THE INVENTION

Ultrasound screening is a well-established method for monitoring fetal development in the uterus, where besides 2D US this includes Doppler, color Doppler and 3D acquisitions with different transducers. During the examination the sonographer determines fetal age and the number of fetuses, and either identifies abnormalities of fetus, placenta or uterus or, in most cases, confirms normal development. This is done at several stages during gestation and always starts with getting an overview of the normal anatomy of the fetus: its general outer appearance; the size, shape and appropriateness of body and extremities; and the orientation, size-relations and flow in the heart.

A quite broad standardization exists for the second trimester scan at 19-22 weeks gestational age (GA). During these scans, many problems can be detected and appropriate actions triggered. A thorough anatomy scanning in the first trimester, at 9-13 weeks GA, is less common; however, it is acknowledged among experts that this enables detection of many problems much earlier than the second trimester scan: Kenkhuis, M. J. A.; Bakker, M.; Bardi, F.; Fontanella, F.; Bakker, M. K.; M K, Fleurke-Rozema, H, Bilardo, C M: Yield of a 12-13 week scan for the early diagnosis of fetal congenital anomalies in the cell-free DNA era, Ultrasound in Obstetrics and Gynecology 2017. The detection of anomalies highly depends on the sonographer following a pre-defined protocol agreed by experts, so knowledge of, and training on, following the protocol is essential—both for first and second trimester scans.

While the ultrasound examination itself is always at least 3D (2D cine-sequence, 2D+Doppler, 3D still acquisition or 3D cine-sequence), the saved screenshots are usually 2D plus very few additional 3D screenshots. For the evaluation of fetal anatomy it is highly relevant to select the right 2D plane for biometry measurements and general assessment.

For this, it is important to alter the 2D viewing plane during the examination to get a 3-dimensional impression of the structure examined.

Due to fetal differences, fetal position within the uterus and limitations of the ultrasound imaging, the optimal 2D view cannot always be obtained:

- bones of the fetus or mother may cast shadows on important structures (e.g. the umbilical vein in an abdominal view);
- a specific fetus may have an unusually low umbilical vein, such that it cannot be imaged together with the stomach in a transversal view;
- a very small umbilical vein may be hardly visible; or
- the bladder may simply be empty, such that it cannot be imaged.

The fetus may be moving during the acquisition, such that the sonographer may decide to take a less optimal but sharp 2D image. Even with optimal images, there may be multiple choices of correct 2D planes possible.

Doppler sonography is essential to examine the function of the heart chambers, outflow tracts and other vessels like ductus *venosus*, brain vessels, umbilical cord, placenta and uterine arteries. Here, it is very important to evaluate a time sequence of the moving heart and not just a screenshot saved for documentation. Further, the same restrictions to image selection apply as for 2D screenshots, e.g. bony shadows, fetal specifications, motion etc.

Apart from a general comment on the scanning conditions, there is no documentation on the circumstances under which the images have been acquired, such that retrospectively it is impossible to determine from the screenshots their quality given a specific fetus. This hinders retrospective review, quality control or training. Furthermore, any motion information (e.g. heart Doppler) is missing in current fetal screening documentation.

The role of 3D volumetric ultrasound is also continuously increasing, though the major part of fetal ultrasound scanning is still performed in 2D or 2D+time. For some specific issues like outer malformations, the assessment can be done much better on a 3D rendered view than on 2D cut-planes. Examples of such malformations are cleft lip and palate, *spina bifida* and placenta shape irregularities. Another advantage of 3D ultrasound is the possibility to reconstruct oblique planes, which cannot be imaged natively. An example is the examination of the pelvic floor muscles, which need to be analyzed in a 2D plane parallel to the pelvic floor. The pelvic floor is too deep in the pelvis to acquire adequate images with trans-abdominal 2D ultrasound, and 2D trans-perineal planes are perpendicular to the plane in question. With 3D trans-perineal US (TPUS) an adequate plane can be reconstructed for analysis and diagnosis: A. Youssef, E. Montaguti, O. Sanlorenzo, L. Cariello, G. Salsi, G. Morganelli, C. Azzarone, G. Pilu and N. Rizzo, Reliability of new three-dimensional ultrasound technique for pelvic hiatal area measurement, Ultrasound in Obstetrics and Gynaecology 2016.

Accordingly, for a thorough assessment of a live fetus in utero it would be desirable to be able to provide 2D ultrasound; the 'time' dimension, i.e. moving the scan location through the body and observing motion; Doppler vessel analysis; 3D ultrasound for surface renderings and oblique plane views; and to ensure scan standardization for better comparability and improved detection of abnormalities.

Key to the robust detection of issues during fetal screening is good training of the sonographer to follow a protocol agreed on by experts. Currently, the only way to ensure this quality is by supervision during the task—either in a training environment, or in a daily work environment. Tele-health or remote review of the scanning has to be done in real time, as retrospective quality checking is of limited practicality.

Thus, today, quality management, training, second opinions, and standardization are all limited by the availability of experienced personnel.

Further, assessing the correctness of the US examination by reviewing the generated 2D- or 3D-rendered saved views is hindered by the lack of context, as the motion during the examination is essential to assess the appropriateness of any selected screenshot.

The purpose of the invention is to reduce the reliance on trained sonographers by providing a computer-implemented system and method for creating a US scan record that is appropriately standardized.

US 2016/038121 relates to an ultrasound imaging system configured to receive data from an ultrasound scan, to detect a position and orientation of an anatomical object of interest, to generate a plurality of two-dimensional slices from the data, and to define respective slice locations for the anatomical object of interest so as to obtain a set of two-dimensional standard views of the anatomical object of interest.

SUMMARY OF THE INVENTION

The invention is defined by the claims.

According to examples in accordance with an aspect of the invention, there is provided a system for generating ultrasound data in respect of an anatomical body being scanned, comprising:
an input for receiving a time sequence of 2D and/or 3D ultrasound images of the anatomical body;
a memory which stores a model of the anatomical body which comprises structures of interest of the anatomical body, and stores a predetermined scan protocol specifying a sequence of types of ultrasound scan of the structures of interest;
and a controller which is configured to:
register the received ultrasound images with the model thereby to identify the structures of interest within the ultrasound images;
identify best images for the types of scan of the identified structures of interest specified in the protocol; and
compile the sequence, specified in the protocol, of the best images.

This system enables the images to be standardized as a predetermined protocol for each of a number of different structures of an anatomical body. This is particularly beneficial for first trimester fetal scanning, where standardization has been less common than for second trimester scanning, and for which the detection of many problems is possible much earlier than the second trimester scan. The system thus enables the training of new protocols and standardization. Standardization can improve the robustness and quality of the interpretation of the scans, relying less on the skill of the sonographer, and facilitating second readings of the scans done remotely e.g. by tele-medicine. It can eliminate the need for a second sonographer to be present for quality control. The use of the sequence rather than a whole set of captured ultrasound image data reduces the amount of data to be stored and to be transmitted for remote viewing. The sequence can be in the form of a video recording, and this would be much shorter than the full scan. The standardized sequence and the reduced length make review easier and more efficient.

The predetermined scan protocol specifies a time-ordered sequence of types of ultrasound scan of the structures of interest.

The compiled sequence preferably comprises video snippets each of which is for one of the structures of interest and includes the respective best image as a frame within the video snippet. This establishes the context of the best image.

The anatomical body model is preferably geometric, for example a geometric segmentation model (generated by a segmentation processor), and it preferably includes semantic data such as ontological data like text containing names, relating to the structures of interest. This enables the scans to be registered spatially within the anatomical body such as the placenta or the fetus or the heart of the fetus, and/or to be recognized by labelling with identifications such as the name of a bone or artery.

The controller is preferably configured to register the received ultrasound images with the model to identify the scan types of the structures of interest within the ultrasound images. For example, the saved data from the scan are electronically registered with a model of a fetus in utero. Then when the compiled sequence is viewed, the information relating to the model is also viewable in context. Options for this are screen-labels in the compiled sequence, or a schematic view of the fetus or scan protocol at the boundary of the image.

Further, the controller may be configured to keep track of the acquired sequences during the examination and display visually, how much of the protocol has been covered already and what scans are missing. One embodiment of this is a schematic graphical representation of the protocol, e.g. as a checklist, with scanned items appearing as green and not-yet-scanned items appearing red.

Preferably, the memory is configured to store a plurality of different scan protocols specific to respective types of subject. These can correspond to existing standardized scan sequences e.g. for first and second trimester scans of a fetus. The appropriate protocol can be selected and then used by the system.

Preferably the scan protocol is specific to a human fetus, but there could as well be protocols for the scanning of other anatomical features such as adult organs and bones.

The sequence of types of ultrasound scan of the structures of interest specified in the scan protocol may comprise different view planes and orientations of at least a 2D scan of the subject relative to the model, but optionally or alternatively 3D scans and Doppler and/or color Doppler scans. It may comprise the number and duration and quality of 2D and/or 3D spatial images.

The system may be configured to transmit the compiled sequence for remote viewing, e.g. as a video sequence comprising video snippets each with data, such as labels naming an anatomical feature or a scan type, associating it with the model. This allows a sonographer to review the scan remotely.

From another aspect, the invention provides a computer-implemented method for generating ultrasound data in respect of an anatomical body being scanned, comprising:
receiving a time sequence of at least 2D and/or 3D ultrasound images of the anatomical body;
storing a model of the anatomical body which comprises structures of interest of the anatomical body, and storing a predetermined scan protocol specifying a sequence of types of ultrasound scan of the structures of interest;
registering the received ultrasound images with the model thereby identifying the structures of interest within the ultrasound images;
identifying best images for the types of scan of the identified structures of interest specified in the protocol; and
compiling the sequence, specified in the protocol, of the best images.

The compiled sequence preferably comprises video snippets each of which is for one of the structures of interest and includes the respective best image as a frame within the video snippet.

The invention also provides such a method comprising using any of the systems described above.

From another aspect, the invention provides a computer program product comprising a computer readable storage medium having computer readable program instructions embodied therewith for, when executed on an image processor of a system as described above, cause the image processor to implement the method described above. Consequently, an existing ultrasound imaging processing apparatus may be reconfigured or upgraded using such a computer program product to implement the method of the present invention.

The protocols can readily be updated e.g. by providing ROM or data transmissions of files storing the updates, and loading them into the system.

These and other aspects of the invention will be apparent from and elucidated with reference to the embodiment(s) described hereinafter.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
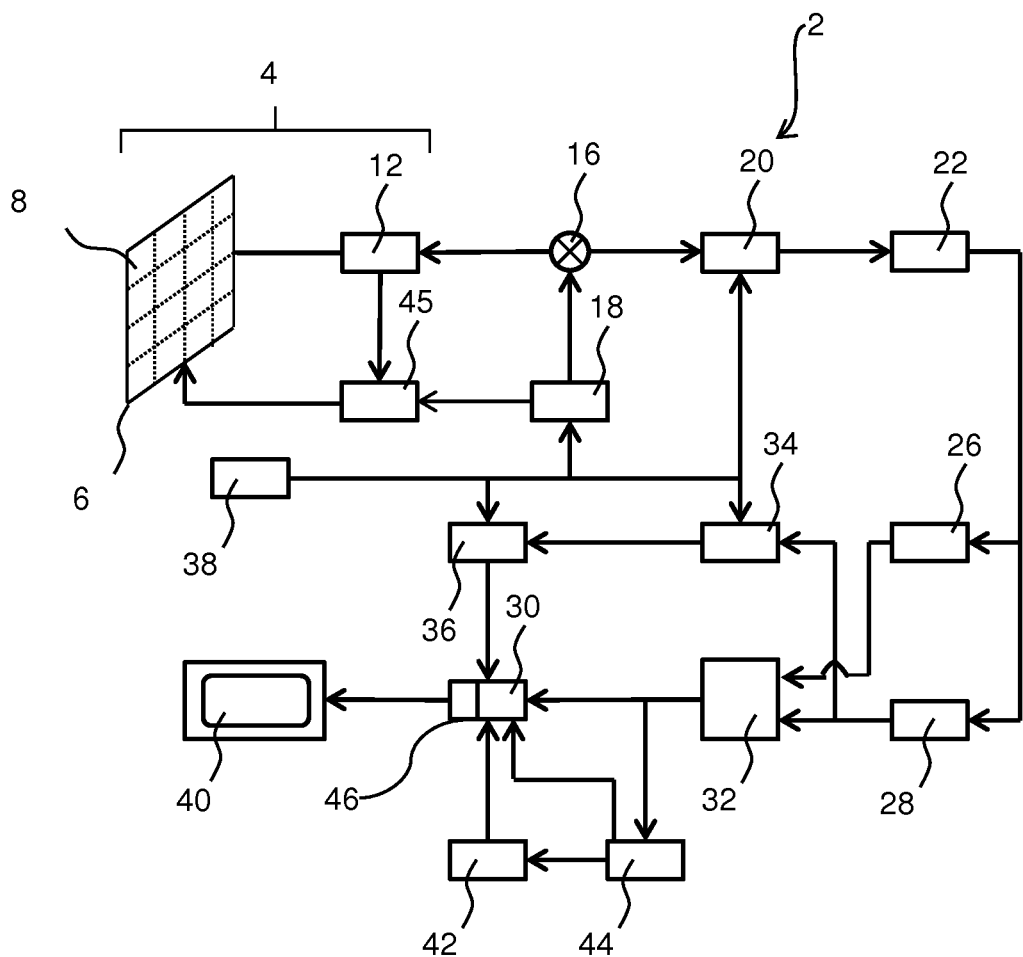
FIG. 1 is a schematic block diagram of an embodiment of an ultrasound imaging system with an array transducer according to an embodiment.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a system (and method) for generating ultrasound data in respect of an anatomical body being scanned, which makes use of a predetermined scan protocol. This protocol specifies a sequence of types of ultrasound scan of structures of interest. These types may for example be different imaging modalities (static, dynamic, 2D, 3D etc.) which are most appropriate for viewing different structures within the anatomical body. From received ultrasound images, a model is used to identify the structures of interest within the ultrasound images. The best images for creating the types of scan of the protocol are then identified and a sequence is compiled of those best images. In this way, a sequence is created which combines different types of scan, in a structured way according to a predetermined protocol. This makes the analysis of the sequence most intuitive for a user, and simplifies comparison between different sequences.

One example of an application of the invention, which will be discussed below, is to generate a standardized video of a fetal screening examination which enables a retrospective review of the examination. This is achieved with two key technical features: using video snippets instead of screenshots to establish context; and the automated assembly, from full data capture, of the video as a standardized protocol sequence. It enables quality control, second reading (e.g. tele-medicine) and training without the requirement for the live presence of a second sonographer during the examination.

The general operation of an exemplary ultrasound diagnostic imaging system will first be described, with reference to FIG. 1, and with emphasis on the signal processing function of the system since this invention relates to the processing of the signals measured by the transducer array.

The system comprises an ultrasound probe 4, which has a transducer array 6 for transmitting ultrasound waves and receiving echo information. Traditionally, piezoelectric materials have been used for ultrasonic transducers. Examples are lead zirconate titanate (PZT) and polyvinylidene difluoride (PVDF) materials, with PZT being particularly popular as the material of choice. Single crystal piezoelectric materials are used to achieve high piezoelectric and electro-mechanical coupling constants for high performance transducers.

Recent developments have led to the prospect that medical ultrasound transducers can be batch manufactured by semiconductor processes. Desirably these processes should be the same ones used to produce the application specific integrated circuits (ASICs) needed by an ultrasound probe such as a CMOS process, particularly for 3D ultrasound. These developments have produced micro machined ultrasonic transducers or MUTs, the preferred form being the capacitive MUT (CMUT). CMUT transducers are tiny diaphragm-like devices with electrodes that convert the sound vibration of a received ultrasound signal into a modulated capacitance.

CMUT transducers in particular are able to function over a broad bandwidth, enable high resolution and high sensitivity imaging, and produce a large pressure output so that a large depth of field of acoustic signals can be received at ultrasonic frequencies.

In this example, the transducer array 6 is a two-dimensional array of transducers 8 capable of scanning either a 2D plane or a three dimensional volume for 3D imaging. In another example, the transducer array may be a 1D array, and it may be a 1D array mechanically able to sweep to acquire a sequence of planes for reconstruction of a 3D image.

The transducer array 6 is coupled to a microbeamformer 12 in the probe which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is entirely optional. The examples described below assume that no analog beamforming is performed by the probe.

The microbeamformer 12 is coupled by the probe cable to a transmit/receive (T/R) switch 16, which switches between transmission and reception modes, and protects a main receive beamformer 20 from high energy transmit signals in the case where a microbeamformer is not used and the transducer array is operated directly by the main system beamformer. The transmission of ultrasound beams from the transducer array 6 is directed by a transducer controller 18 coupled to the microbeamformer by the T/R switch 16 and a main transmission beamformer (not shown), which receives input from the user's operation of the user interface or control panel 38.

In a typical line-by-line imaging sequence, the beamforming system within the probe may operate as follows. During transmission, the beamformer (which may be the microbeamformer or the main system beamformer depending upon the implementation) activates a sub-aperture of the transducer array. The sub-aperture may be a one dimensional line of transducers or a two dimensional patch of transducers within the larger array. In transmit mode, the focusing and steering of the ultrasound beam generated by a sub-aperture are controlled as described below.

Upon receiving the backscattered echo signals from the subject, the received signals undergo receive beamforming (as described below), in order to align the received signals, and the sub-aperture is then shifted, for example by one transducer element. The shifted sub-aperture is then activated and the process repeated until all of the transducer elements of the transducer array have been activated. For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 18 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

The transducer controller 18 can be coupled to control a DC bias control 45 for the transducer array. The DC bias control 45 sets DC bias voltage(s) that are applied to the transducer elements.

For each transducer element of the transducer array, analogue ultrasound signals, typically referred to as channel data, enter the system by way of the reception channel. In the reception channel, partially beamformed signals are produced from the channel data by the microbeamformer 12 and are then passed to the main receive beamformer 20 where the partially beamformed signals from individual patches of transducers are combined into a fully beamformed signal, referred to as radio frequency (RF) data. The beamforming performed at each stage may be carried out as described above, or may include additional functions. For example, the main receive beamformer 20 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 22. The signal processor 22 can process the received echo signals in various ways, such as: band-pass filtering; decimation; I and Q component separation; and harmonic signal separation, which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 1 only the receive elements of the microbeamformer 12 and the main receive beamformer 20 are shown, for simplicity. In the complete system, there will also be a transmission chain with a transmission micro beamformer, and a main transmission beamformer.

The function of the microbeamformer 12 is to provide an initial combination of signals in order to decrease the number of analog signal paths. This is typically performed in the analog domain.

The final beamforming is done in the main receive beamformer 20 and is typically after digitization.

The transmission and reception channels use the same transducer array 6 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g. the harmonics of the main harmonic).

The RF signals may then be coupled to a B mode (i.e. brightness mode, or 2D imaging mode) processor 26 and a Doppler processor 28. The B mode processor 26 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 28 processes temporally distinct signals arising from tissue movement and blood flow for the detection of moving substances, such as the flow of blood cells in the image field. The Doppler processor 28 typically includes a wall filter with parameters set to pass or reject echoes returned from selected types of materials in the body.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B mode and Doppler processors are coupled to a scan converter 32 and a multi-planar reformatter 44. The scan converter 32 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 40. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. There is preferably also more permanent storage to allow export of all data. The imaging processor may be adapted to remove certain imaging artifacts from the final ultrasound image, such as: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow in addition to structural measurements such as the sizes of organs and gestational age. The quantification processor may receive input from the user interface 38, such as the point in the anatomy of an image where a measurement is to be made.

Output data from the quantification processor is coupled to a graphics processor 36 for the reproduction of measurement graphics and values with the image on the image display 40, and for audio output from the image display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transducer controller 18 to control the generation (transmission) of ultrasound signals from the transducer array 6 and hence the images produced by the transducer array and the ultrasound system. The transmit control function of the transducer controller 18 is only one of the functions performed. The transducer controller 18 also takes account of the mode of operation (given by the user) and the corresponding required transmitter configuration and band-pass configuration in the receiver analog to digital converter. The transducer controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

As will be understood by the skilled person, the above embodiment of an ultrasonic diagnostic imaging system is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the microbeamformer 12 and/or the Doppler processor 28 may be omitted, the ultrasound probe 4 may not have 3D imaging capabilities and so on. Other variations will be apparent to the skilled person.

The image processor 30 may be provided with a segmentation unit 46 for segmenting anatomical structures in the field of view, such as the fetus, in 2D or 3D ultrasound data captured by the ultrasound probe 4. The segmentation unit 46 then provides segmentation data of the anatomical structures of the fetus. For example, an orientation detection unit (not shown) may be provided for detecting the relative orientation of target anatomical structures of the fetus based on the segmentation data provided by the segmentation unit 46, e.g. within a defined coordinate system such as a thoracic coordinate system. For example, the orientation detection unit may be configured to detect the orientation axis of the fetal spine and the orientation axis of the fetal heart.

By way of example only, the segmentation unit 46 first calculates the orientation axis of the fetal chest in a defined coordinate system from a temporal sequence of ultrasound images. This calculation may be performed on one or more of the ultrasound images of the temporal sequence. The segmentation unit 46 delineates the chest region of the fetus in one or more of the ultrasound images of said temporal sequence. Any suitable segmentation algorithm, such as for example a Hankel transformation algorithm and a deformable contour segmentation algorithm may be used for this purpose. As such algorithms are well-known per se, this will not be explained in further detail for the sake of brevity only.

The processor arrangement for example may be arranged to recognize a vertebra structure, e.g. a part of the fetal spine, within the delineated fetal chest region. The ultrasound image processing apparatus 2 may be trained to develop this functionality using machine learning algorithms such as a random forest algorithm, a deep learning approach or any other suitable learning method in which the processor arrangement is presented with a plurality of fetal images from which the fetal position and associated position of the fetal chest region and the portion of the fetal spine within the fetal chest region is identified.

As explained above, the system 2 generates a standardized video of a fetal screening examination which enables a retrospective review of the examination. This is achieved with two key technical features: using video snippets instead of screenshots to establish context; and the automated assembly, from full data capture, of the video as a standardized protocol sequence. It enables quality control, second reading (e.g. tele-medicine) and training without the requirement for the live presence of a second sonographer during the examination.

This involves the collection and saving in storage of information during a scan, such as 2D video sequences, Doppler images and records, 3D sequences, 3D reconstructed slides, measurements (e.g. of anatomical dimensions or volumes), and other data that may be required in the future. The system electronically performs a registration of the saved data with a model of the fetus in utero. This adds necessary information to the saved data, such as spatial location and the names of anatomical features, and the type of scan. The system assembles a 2D/3D plus time standardized video sequence to comprise all the steps defined in a standardized screening protocol, from the saved data supplemented with the information through the registration with the model. Video-snippets are each formed from a best quality image and its temporally neighboring images. The supplemented saved data records of different scan types are each used to generate the video snippets, and the video snippets are assembled according to the appropriate selected standardized protocol. Any missing snippets can be replaced with appropriate blank snippets or a display of information about what is missing, and the missing snippets can be obtained later and inserted in the video sequence.

These computations are performed by the image processor 30 or by a dedicated processor in addition to the image processor. The scan data are stored in a memory forming part of the image processor 30.

The information capturing includes 2D US video sequences; Doppler imaged sequences or heart rate monitoring with Doppler; 3D acquired full volumes; renderings or 2D viewed (reconstructed or native) slices from 3D acquired volumes; measurements for on-screen display from 2D- or 3D-acquired US, e.g. femur length, nuchal translucency, head diameters, etc.; and labelling (if available from these measurements), for presentation in the screen display.

The model of the fetus in utero should include all the structures that are to be imaged during the examination according to the protocol, such as the fetus, placenta, uterus, full uterus content, uterine arteries, cervix, and fallopian tubes. The preferred model contains both a geometrical representation of the data and a semantic representation (like an ontology) suited to represent the scanning protocol in a schematic way. The geometric model and the semantic model are linked.

The anatomical model for use in the invention could be a standard model, but in the example of the fetus may differ with respect to gestational age and may offer several mutually exclusive variations in some anatomical regions, e.g. male/female outer appearance at the pelvis, or normal or malformed spine. A model in this sense is not one instance of a potential fetus, but a location-specific and labelled collection of variations. Thus in the pelvic region both penis and vulva exist in the model, and the current fetus being scanned will only be associated with one of them.

The model may be obtained by the system 2, for example from storage in the memory of the image processor 30 or as a data input from an external data source (not shown in FIG.

1). Alternatively, it may be generated by the segmentation unit 46 from scanned images.

The registration of the captured and saved data to the geometric and semantic model can mean the localization and orientation of the data in the geometric model and the association of the acquired data with the semantic ontology model. This is performed as follows:

Based on captured labelled measurements, a text-based association to the semantic model is possible, which allows an association with the geometric model. This form of computer-implemented association is known in the art.

For non-labelled acquired data, an image-based association to the geometric model is performed, which enables the relation to the semantic model to be made. Technologies to enable this include: classification of 2D US images, e.g. as described in Christian Baumgartner, Konstantinos Kamnitsas, Jacqueline Matthew, Sandra Smith, Bernhard Kainz, Daniel Rueckert, Real-time Standard Scan Plane Detection and Localisation in Fetal Ultrasound using Fully Convolutional Neural Networks, MICCAI 2006; landmark localization; and structure localization and structure segmentation in medical images, e.g. as described in Schmidt-Richberg A., Brosch T., Schadewaldt N., Klinder T., Peters J., Lorenz C., Abdomen segmentation in 3D fetal ultrasound using CNN-powered deformable models, submitted to MICCAI-workshop on Fetal and Infant analysis (FIFI) 2017.

For labelled data with geometrical content (e.g. a 2D slice with line measurement) a first alignment with the semantic model can be used as an initialization for a second alignment with the geometric model. This makes many image based algorithms much more robust.

For non-labelled data in the vicinity of labelled data, e.g. the 2D slices acquired before and after a measurement, the geometric and semantic registration should be based on the registration of the labelled data in the vicinity. Either it can be directly inferred from the labelled data, or the registration to the model can be used as an initialization for further localization as in the description above for non-labelled acquired data.

The result of the registration process is a localization of each item of captured information in the geometrical and semantic model. By way of first example, a 2D ultrasound image of a femur with a femur length measurement is associated with the structure "femur" in the ontology and the geometric location of the femur below the pelvis and above the foreleg in the geometrical model. As a second example, a 2D+time sequence of the heart without any measurement can be classified as a heart image by deep learning, then associated with the geometric location of the heart and the structure "heart" in the ontology, but also with all concepts of congenital heart disease. A Doppler sequence and a heart-rate graph acquired at the same time are associated with the same structure and location, but also with the semantic terms "Doppler" or "heart-rate-graph". As a third example, a 3D US sequence with a rendering of the face to examine whether a cleft lip/palate can be excluded would be registered to the head of the geometric model. The rendering would then be associated with the structure "face" but also to the concepts "cleft lip/palate". The 3D US volume would be associated with all concepts and structures in the head covered in the volume.

The captured data are also analyzed by the image processor 30 to identify the best image within each temporal sequence of images, for the required type of scan according to one part of the protocol. This may be done according to a measurement done by the sonographer, or the image contrast or texture and/or its spatial location relative to the model, for example. For each best image, temporally adjacent images are preferably added, to form a video snippet, preferably with the best image at the center.

In other words, instead of showing a sequence of individual 'optimal' or best images, short video sequences before and after the 'optimal' image are shown—not only for 2D but also for 3D renderings. This has several advantages: for US, a context awareness is necessary to put a given 2D slice into context. With a short 2D video sequence, the sonographer's process for establishing context is shown and is reviewable—both for quality review and for understanding the image. The same is true for 3D renderings: a short video sequence establishes context, much more than a single screenshot. For some applications, a video sequence is necessary anyway, e.g. for heart motion.

Figure 2:
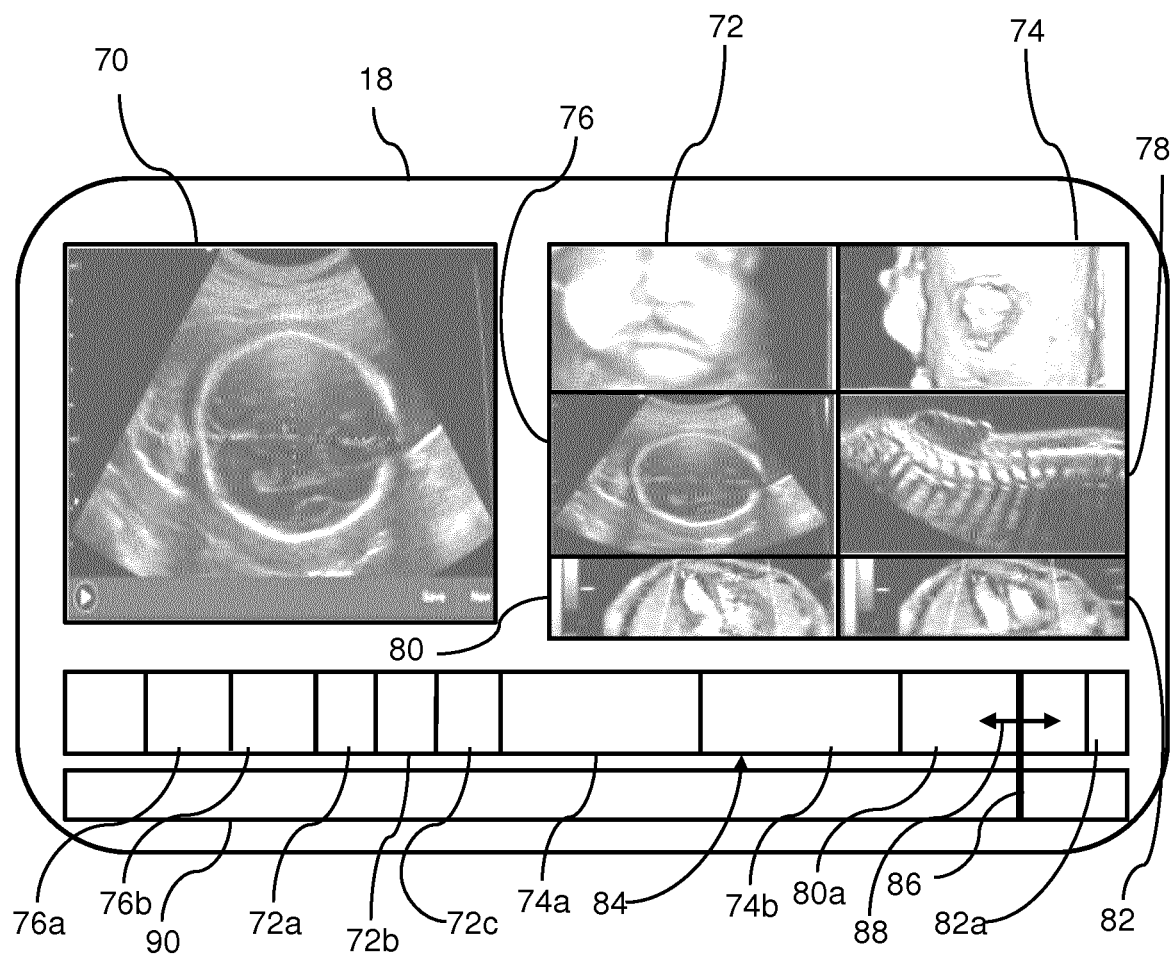
FIG. 2 is a screen display on a display of FIG. 1 and produced in accordance with the embodiment.

The assembly of the video sequence by the image processor 30 or other processor will now be described, with reference to FIG. 2 which is a screen shot of a rendered video sequence for display on the image display 40 or on a different dedicated display (not shown). The video display may be generated by software in the image processor 30. The video sequence may also be transmitted to another device for interactive playback display e.g. for a second review.

The video display represented as a screen shot on the image display 40 has discrete regions for displaying different types of image. A current scan of a head with a representation of head diameters in an optimal plane is displayed in a relatively large area 70. Adjacent to this is a matrix of six display areas. This area may additionally show a scroll-bar to allow many more display regions than six, such that for each item of the protocol a representative image can be shown.

Area 72 displays a surface rendering of a face showing a cleft lip. Area 74 displays a surface rendering of a spine showing *spina bifida* in 3D US. Area 76 displays a smaller scale view of the head of area 70. Area 78 displays a 2D reconstruction of the 3D US image of the spine of area 74. Areas 80 and 82 display two simultaneous images from Doppler examination of the heart, area 80 with a relatively low PRF of 18 cm/s and area 82 with a higher PRF of 44 cm/s.

The video snippets according to the protocol are assembled into a steady video stream which is displayed in the elongate area 84, with time progressing from left to right. In this example, two snippets 76*a* and 76*b* of the image in area 76 are followed by three snippets 72*a*, 72*b* and 72*c* of the image in area 72, followed by two snippets 74*a* and 74*b* of the image in area 74. This is followed by Doppler snippets 80*a* from area 80 and 82*a* from area 82.

The brightness of the video is displayed in area 90, as a function of time in the video sequence.

A moment in time during playback is selectable through a user interface such as a GUI on the control panel 38 or another interface device (not shown), by moving a vertical line cursor 86 in the forward or backward direction shown by arrow 88. This can be used to view the snippet in the enlarged area 70. It can also be used for editing the sequence, for example to fill in any missing snippets. As explained above, any snippets required by the protocol that are currently unavailable can be replaced by a blank snippet or other marker in the sequence. This can also be illustrated in the screenshot area 72-82 by showing e.g. a white screenshot with a label.

Thus a standard scanning protocol for a fetal screening is associated with semantic terms (e.g. femur length) and geometric locations (e.g. sagittal scan through femur bone).

Then, a standard order and presentation of the protocol is encoded in the semantic representation. The video sequence is assembled to show one item after the other of the protocol.

The overall video is much shorter than viewing a full recording of the scan. By organizing the video sequence according to a protocol, the video sequences are comparable, which has several advantages: it is easier and more efficient for a viewer to review, as the order is fixed; and missing parts can be quickly assessed and remarked, also during scanning. The sequence review can be used for training or quality control. The fixed order here also helps to establish the protocol and may be used to devise new protocols. Protocol changes may be much easier to establish by issuing a new version of the video assembly, than by certifying all sonographers. When during capture of the US examination the acquisition of the necessary video parts according to protocol are tracked, so that the user can be informed of what is completed and what is missing on a simple check-mark panel. This also helps to establish a protocol. Benefits can be gained by adding information on transducer positioning, e.g. in 3D graphics or color-coded graphics, for each video-snippet.

Additional consistency checking of different US modality acquisitions, e.g. 2D with 3D with Doppler, etc., can be added after the semantic localization of the scans to the same terms.

Ideally, the video sequence automation runs in parallel to the scan, i.e. simultaneously, such that a checklist can be kept at the side of the screen, showing the operator which parts have already been acquired and which have not. It also enables manual interaction, in case the classifier does not recognize a certain view, e.g. because of severe malformations or image quality issues. Further, the operator is able to add screenshots of malformations to the protocol, which would not necessarily appear in a standardized sequence. However, any malformations should be attributable to an anatomy/ontology and will thus be displayed in the sequence at the logical position, where this anatomy appears. As an example, if a large gall bladder cyst is found, typing "gall bladder" as a title should yield, as a search term in the ontology, that this belongs to the liver, and the screen shot should be shown after the normal liver view.

If the scan sequence is assembled after the scan procedure, as a minimum requirement a review by the operator is necessary, to correct it if necessary, e.g. semi-automatically by adding a view, that was acquired but was not classified correctly, or adding screenshots of malformations. To reduce workload, the review can be restricted to the saved 2D screenshots, as the sonographer is expected to take screenshots of any normal anatomy to document or any identified malformation.

In case certain views cannot be obtained, or have not been obtained when the video sequence is established retrospectively, an appropriate blank frame may appear, e.g. black with standardized words or a schematic view of the structure not obtained, e.g. in a different color, e.g. red, and stationary. This will convey the message quickly and clearly that this view has not been acquired, while keeping the same video sequence flow that is consistent i.e. standardized for all patients.

It may be possible to review the video directly after the scan, i.e. together with the mother, and to re-acquire missing frames directly after that on the couch. However, it is a realistic scenario that not all scans can be obtained e.g. due to fetal position (e.g. flexed neck prevents proper NT measurement), and a missing scan should thus be considered a regular incident. Unless there are other abnormality findings or specific risks, this would not be followed up until the next regular scan.

Examples of standard protocols that may be used in the invention include the protocol described as the Routine Ultrasound Worksheet (Example) in the Appendix on page 113 of Kenkhuis, M. J. A.; Bakker, M.; Bardi, F.; Fontanella, F.; Bakker, M. K.; M K, Fleurke-Rozema, H, Bilardo, C M: Yield of a 12-13 week scan for the early diagnosis of fetal congenital anomalies in the cell-free DNA era, Ultrasound in Obstetrics and Gynecology 2017, the publication referred to above. It specifies the required measurements in order to reach clinical conclusions based on the sonographic appearance of the fetal anatomy and the GA interpreted using these measurements. The measurements are crown-rump length, nuchal translucency, biparietal diameter, head circumference, abdominal circumference and femoral diaphysis length.

Other detailed scanning protocols for 1st and 2nd trimester are for example published by the ISUOG (International Society for Ultrasound in Obstetrics and Gynaecology) as:

Ultrasound Obstet Gynecol 2013; 41: 102-113, published online in Wiley Online Library (wileyonlinelibrary.com). DOI: 10.1002/uog.12342, ISUOG Practice Guidelines: performance of first-trimester fetal ultrasound scan;

and also as:

Ultrasound Obstet Gynecol (2010), published online in Wiley Online Library (wileyonlinelibrary.com). DOI: 10.1002/uog.8831, Practice guidelines for performance of the routine mid-trimester fetal ultrasound scan. http://onlinelibrary.wiley.com/doi/10.1002/uog.12342/pdf https://www.isuog.org/uploads/assets/uploaded/c60cd864-13f2-4e12-a4fd7883284058fd.pdf.

Taking these into account, an example for a first-trimester scanning protocol could be as follows:

sagittal section of embryo with measurement of Crown-Rump-Length (CRL);
symmetrical largest true axial view of the head with measurements of the biparietal diameter (BPD) and head circumference (HC);
nuchal translucency (NT) visualization and measurement in non-flexed standardized view;
if embryo >10 weeks GA: visualize midline third ventricle, interhemispheric fissure and choroid plexus;
if embryo >13 weeks GA: visualize thalamus;
sagittal view of face;
longitudinal and axial views of the spine;
sweep through the thorax establishing normal, homogenous lungs, diaphragmatic continuity, and normal intra-abdominal position of liver and spleen; this sweep would fully become part of the established video sequence
normal heart position;
sweep through fetal abdomen, establishing appearance of stomach, kidneys and bladder, as well as umbilical chord insertion; (as above, full sweep in final video)
limbs: each upper and lower limb should be established, as well as presence of both hands and feet;
evaluate placenta appearance and position (with limited consequences, as it may migrate away);
in patients with prior caesarean section, the scar should be evaluated.

This is the current first trimester protocol scan. An algorithm would then be trained to classify obtained views of fetuses to the classes (more than 20) and label the structures of interest.

According to this embodiment of the invention, the Crown-rump length (CRL) measurement would then be embedded in a short video sequence (snippet) showing more of the fetus before and after the optimal plane has been frozen, and displaying the measurement on top, together with a reference range and fetal-age estimation. Biparietal diameter (BPD), head circumference (HC) and nuchal translucency (NT) would be visualized similarly. For the structures in the first-trimester scanning protocol immediately above, from the fourth listed entry of the protocol (midline third ventricle, interhemispheric fissure and choroid plexus) onwards, the classification of the frames and localization of the structures is sufficient, and would be displayed. If a sweep is needed to establish normality of a structure, e.g. the lungs in the sweep through the thorax, a standardized sweep should be part of the video sequence, i.e. always starting from the top, not repeating any frames, and going at a fixed speed through the lung from top to bottom.

Once an extended first trimester scan becomes standard in the future, it is likely that additional structures similar to a second trimester scan, like abdominal circumference (AC), femur length (FL), humerus length (HL), and detailed heart measurements (visualization of inflow/outflow tract, 4-chamber view, . . . ) will be included.

For a second trimester scan, the protocol would be similar, but much more extended. The protocols will be apparent for example from the A. Youssef et al reference above.

The protocol would be specific for a gestational age range, e.g. the protocol described above would be applicable for a GA of 11-14 weeks, and there would be a different second trimester screening protocol for 18-24 weeks with different classifiers. As the GA is established during the scan anyway via standard measurements, and with a repeat scan a predetermined value is known anyway, this can be assumed to be available at the beginning of the procedure, such that the appropriate protocol and thus the appropriate video-sequence automation would be selected automatically.

Current scanning protocols require purely 2D imaging. However, the use of 3D US is increasing, with (non-standard) applications to visualize the baby's face, to automate biometry, or to evaluate the 3D appearance of potential malformations, e.g. spine *bifida* or ear-shape. A limited set of likely 3D acquisitions (e.g. face, ear, *spina bifida*, navel insertion) could be added to the classifier and displayed at the appropriate sections of the scan, i.e. the 3D face acquisition after the 2D sagittal one, the ear after the head assessment.

Detailed descriptions of how to obtain the specific views can be found in the references given above, or for example here: https://www.ncbi.nlm.nih.gov/pmc/articles/PMC5029995/, Bethune, M, et al. "A pictorial guide for the second trimester ultrasound", Australas J US Med 2013 Aug. 16(3): 98-113.

Figure 3:
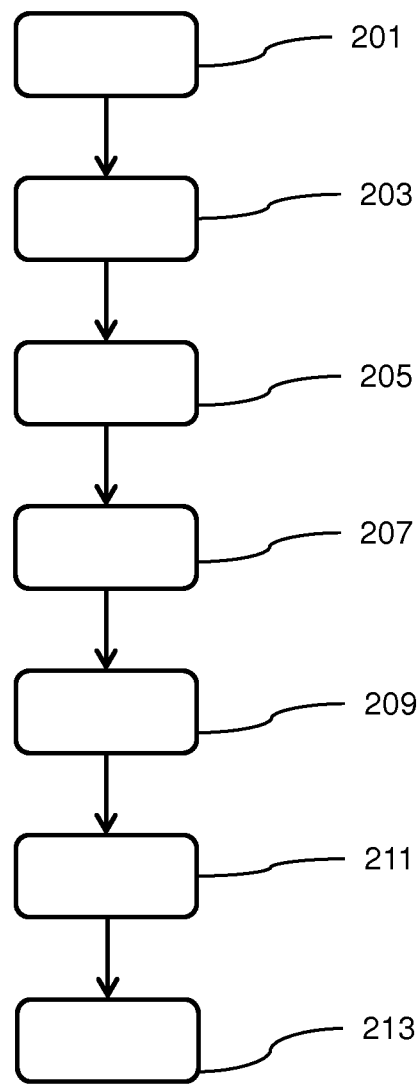
FIG. 3 is a flowchart of a computer-implemented method according to the embodiment.

FIG. 3 is a flowchart of a computer-implemented method 200 according to the embodiment. In step 201, the system 2 captures the 2D, 3D or Doppler data and displays the corresponding images on the image display 40. In step 203, the system 2 acquires and stores the geometric and semantic model that corresponds to the subject being scanned, and also the appropriate protocol for the compilation of the video sequence. In step 205, which may proceed in parallel with step 201, the system 2 registers the captured data with the model, so as to store the associations between the captured data and the model both geometrically and semantically. In step 207, the system processes the captured data to identify the best image(s) for each of the types of scan required by the protocol. In step 209, the system generates a video snippet for each of the best images, and in step 211 it assembles the snippets into a single video sequence which is stored. In step 213, once any editing of the video sequence has been completed and any repeat scans captured and processed and inserted into the sequence, the video sequence is transmitted to an external server for second review, and is also made available for review locally at the system 2. The original full data set of the whole examination may then be deleted or archived.

The above described embodiments of the computer-implemented method 200 may be realized by computer readable program instructions embodied on a computer readable storage medium having, when executed on a processor arrangement of the ultrasound image processing apparatus 2, cause the processor arrangement to implement the computer-implemented method 200. Any suitable computer readable storage medium may be used for this purpose, such as for example an optically readable medium such as a CD, DVD or Blu-Ray disc, a magnetically readable medium such as a hard disk, an electronic data storage device such as a memory stick or the like, and so on. The computer readable storage medium may be a medium that is accessible over a network such as the Internet, such that the computer readable program instructions may be accessed over the network. For example, the computer readable storage medium may be a network-attached storage device, a storage area network, cloud storage or the like.

The computer readable storage medium may be an Internet-accessible service from which the computer readable program instructions may be obtained. In an embodiment, an ultrasound image processing apparatus 2 is adapted to retrieve the computer readable program instructions from such a computer readable storage medium and to create a new computer readable storage medium by storing the retrieved computer readable program instructions in a data storage arrangement, e.g. in a memory device or the like forming part of the data storage arrangement, which data storage arrangement is accessible to the processor arrangement of the ultrasound image processing apparatus 2 such that the processor arrangement can retrieve the computer-readable program instructions from the data storage arrangement for execution.

It will be appreciated that many variations of the apparatus and method are possible, within the scope of the invention as claimed.

Although the standardized protocol is especially useful for scanning the human fetus, or the fetal heart, other protocols may be used for scanning other anatomical subjects such as organs. Any type of ultrasound scanning may be used. Any suitable criteria for selecting the best images may be used, and these criteria may be variable by user input or according to the protocol itself. The video sequence need not comprise snippets, but could alternatively comprise sequences of multiple satisfactory images, not necessarily adjacent spatially or temporally, and they may be still images; Doppler data could be presented in many different ways to show the most significant regions where motion is occurring.

The model may take any of a wide variety of forms, and the spatial information in the model need not be derived from a geometric segmentation but could be from another synthesis or from actual measurements e.g. using Doppler data and 3D volumetric images. The semantic part of the model could comprise any form of information such as alphanumeric codes or human-readable text, and could represent the type of scan and/or the anatomical feature that has been scanned and identified.

The protocol may specify any of a wide variety of characteristics of a scan, such as the type, number, duration and quality of the imaging.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A system for generating ultrasound data in respect of an anatomical body being scanned, comprising:
an input for receiving a time sequence of 2D and/or 3D ultrasound images of the anatomical body;
a memory which stores a model of the anatomical body which comprises structures of interest of the anatomical body, and stores a predetermined scan protocol specifying a sequence of types of an ultrasound scan of the structures of interest, the sequence having a fixed order; and a controller which is configured to:
register the received ultrasound images with the model thereby to identify the structures of interest within the ultrasound images;
identify target images for the types of scan of the identified structures of interest specified in the protocol; and
compile the sequence with the fixed order, specified in the protocol, of the target images, the compiled sequence taking the form of a video sequence, the video sequence comprising video snippets each of which is for one of the structures of interest and comprises a respective best image as a frame within the video snippet, the video snippets assembled according to the fixed order of the scan protocol.

2. The system according to claim 1, wherein the anatomical body model is geometric and comprises semantic data relating to the structures of interest.

3. The system according to claim 2, wherein the anatomical body model comprises a geometric segmentation model.

4. The system according to claim 1, wherein the controller is configured to register the received ultrasound images with the model to identify the scan types of the structures of interest within the ultrasound images.

5. The system according to claim 1, wherein the memory is configured to store a plurality of different scan protocols specific to respective types of subject.

6. The system according to claim 1, wherein the scan protocol is specific to a human fetus.

7. The system according to claim 1, wherein the sequence of types of the ultrasound scan of the structures of interest specified in the scan protocol comprises different view planes and orientations of at least a 2D scan of the subject relative to the model.

8. The system according to claim 1, wherein the sequence of types of the ultrasound scan of the structures of interest specified in the scan protocol comprises a number, a duration and a quality of 2D and/or 3D spatial images.

9. The system according to claim 1, wherein the sequence of types of the ultrasound scan of the structures of interest specified in the scan protocol comprises Doppler and/or color Doppler video images.

10. The system according to claim 1, wherein the system is configured to transmit the compiled sequence for remote viewing.

11. A computer-implemented method for generating ultrasound data in respect of an anatomical body being scanned, the method comprising:
receiving a time sequence of at least 2D and/or 3D ultrasound images of the anatomical body;
storing a model of the anatomical body which comprises structures of interest of the anatomical body, and storing a predetermined scan protocol specifying sequence of types of an ultrasound scan of the structures of interest, the sequence having a fixed order;
registering the received ultrasound images with the model thereby identifying the structures of interest within the ultrasound images;
identifying target images for the types of scan of the identified structures of interest specified in the protocol; and
compiling the sequence with the fixed order, specified in the protocol, of the target images, the compiled sequence taking the form of a video sequence, the video sequence comprising video snippets each of which is for one of the structures of interest and comprises a respective best image as a frame within the video snippet, the video snippets assembled according to the fixed order of the scan protocol.

12. The method according to claim 11, wherein the compiled sequence comprises video snippets each of which is for one of the structures of interest and comprises the respective target image as a frame within the video snippet.

13. A computer program product comprising a tangible, non-transitory computer readable storage medium having computer readable program instructions embodied therewith for, when executed on an image processor, causes the image processor to:
receive a time sequence of at least 2D and/or 3D ultrasound images of an anatomical body;
store a model of the anatomical body which comprises structures of interest of the anatomical body, and store a predetermined scan protocol specifying a sequence of types of an ultrasound scan of the structures of interest, the sequence having a fixed order;
register the received ultrasound images with the model thereby identifying the structures of interest within the ultrasound images;
identify target images for the types of scan of the identified structures of interest specified in the protocol; and
compile the sequence with the fixed order, specified in the protocol, of the target images, the compiled sequence taking the form of a video sequence, the video sequence comprising video snippets each of which is for one of the structures of interest and comprises a respective best image as a frame within the video snippet, the video snippets assembled according to the fixed order of the scan protocol.

14. The computer program product according to claim 13, wherein the anatomical body model is geometric and comprises semantic data relating to the structures of interest.

15. The computer program product according to claim 14, wherein the anatomical body model comprises a geometric segmentation model.

16. The computer program product according to claim 13, wherein the processor is further configured to register the received ultrasound images with the model to identify the scan types of the structures of interest within the ultrasound images.

17. The computer program product according to claim 13, wherein a memory is configured to store a plurality of different scan protocols specific to respective types of subject.

18. The computer program product according to claim 13, wherein the sequence of types of the ultrasound scan of the structures of interest specified in the scan protocol comprises different view planes and orientations of at least a 2D scan of the subject relative to the model.

19. The computer program product according to claim 13, wherein the sequence of types of the ultrasound scan of the structures of interest specified in the scan protocol comprises a number and duration and quality of 2D and/or 3D spatial images.

20. The computer program product according to claim 13, wherein the sequence of types of the ultrasound scan of the structures of interest specified in the scan protocol comprises Doppler and/or color Doppler video images.

\* \* \* \* \*